US011661464B2

(12) United States Patent
Choi et al.

(10) Patent No.: US 11,661,464 B2
(45) Date of Patent: May 30, 2023

(54) PROTEIN TRANSDUCTION DOMAIN, FUSION COMPOUND CONTAINING THE SAME, AND PHARMACEUTICAL COMPOSITION CONTAINING THE FUSION COMPOUND

(71) Applicant: GENESEN CO., LTD., Seoul (KR)

(72) Inventors: Soo-Young Choi, Chuncheon-si (KR); Jin-Seu Park, Chuncheon-si (KR); Kyuhyung Han, Chuncheon-si (KR); Keunwook Lee, Seoul (KR); Jong Kook Park, Chuncheon-si (KR); Sunghou Lee, Yongin-si (KR); Sung Ho Lee, Seoul (KR); Soojung Park, Incheon (KR); Won Sik Eum, Chuncheon-si (KR); Min Jea Shin, Incheon (KR); Hyeon Ji Yeo, Seoul (KR); Eun Ji Yeo, Seoul (KR); Yeon Joo Choi, Chungcheongbuk-do (KR); Eun Jeong Sohn, Namyangiu-si (KR); Hyun Ju Cha, Dongducheon-si (KR); Hyun Jung Kwon, Gangneung-si (KR); Dae Won Kim, Gangneung-si (KR)

(73) Assignee: Genesen Co., Ltd., Seoul (KR)

( * ) Notice: Subject to any disclaimer, the term of this patent is extended or adjusted under 35 U.S.C. 154(b) by 194 days.

(21) Appl. No.: 17/086,031

(22) Filed: Oct. 30, 2020

(65) Prior Publication Data

US 2021/0355240 A1    Nov. 18, 2021

(51) Int. Cl.
| | | |
|---|---|---|
| *C07K 19/00* | (2006.01) | |
| *C07K 14/47* | (2006.01) | |
| *A61K 8/64* | (2006.01) | |
| *A61K 38/00* | (2006.01) | |

(52) U.S. Cl.
CPC .......... *C07K 19/00* (2013.01); *C07K 14/4702* (2013.01); *A61K 8/64* (2013.01); *A61K 38/00* (2013.01); *C07K 2319/01* (2013.01)

(58) Field of Classification Search
CPC ...... C07K 19/00; C07K 14/4702; A61K 8/64; A61K 38/00
See application file for complete search history.

(56) References Cited

FOREIGN PATENT DOCUMENTS

| | | | |
|---|---|---|---|
| JP | 2015-523966 A | 8/2015 | |
| KR | 10-2002-0067108 A1 | 8/2002 | |
| KR | 10-0495138 B1 | 6/2005 | |
| KR | 10-0495140 B1 | 6/2005 | |
| KR | 10-1669203 B1 | 10/2016 | |
| KR | 10-2060411 B1 | 12/2019 | |

OTHER PUBLICATIONS

Lee et al., "Tat-biliverdin reductase A protects INS-1 cells from human islet amyloid polypeptide-induced cytotoxicity by alleviating oxidative stress and ER stress", Cell Biology International, vol. 41, No. 5—25 pages ( Mar. 20, 2017).
Kim et al., "Tat-biliverdin reductase A inhibits inflammatory response by regulation of MAPK and NF—KB pathways in Raw 264.7 cells and edema mouse model", Molecular Immunology, vol. 63, No. 2—12 pages (Sep. 17, 2014).
Kim et al., "Tat-Biliverdin Reductase A Exerts a Protective Role in Oxidative Stress-Induced Hippocampal Neuronal Cell Damage by Regulating the Apoptosis and MAPK Signaling", International Journal of Molecular Sciences, vol. 21, No. 8—13 pages (Apr. 11, 2020).
Jung et al., "Phosphoglycerate Mutase 1 Prevents Neuronal Death from Ischemic Damage by Reducing Neuroinflammation in the Rabbit Spinal Cord", International Journal of Molecular Sciences, vol. 21, No. 19—15 pages (Oct. 8, 2020).
Kim et al., "Phosphoglycerate mutase 1 reduces neuronal damage in the hippocampus following ischemia/reperfusion through the facilitation of energy utilization", Neurochemistry International, vol. 133—9 pages (Dec. 10, 2019).
Jung et al., "Phosphoglycerate Mutase 1 Promotes Cell Proliferation and Neuroblast Differentiation in the Dentate Gyrus by Facilitating the Phosphorylation of cAMP Response Element-Binding Protein", Neurochemical Research, vol. 44, No. 2—10 pages (Nov. 20, 2018).
Peinado et al., "Proteomic characterization of nitrated cell targets after hypobaric hypoxia and reoxygenation in rat brain", Journal of Proteomics, vol. 109,—13 pages (Jul. 23, 2014).
Ohba et al., "Phosphoglycerate Mutase 1 Activates DNA Damage Repair via Regulation of WIP1 Activity", Cell Reports., vol. 31, No. 2—22 pages (Apr. 14, 2020).
Zhang et al., "PGAM1 is Involved in Spermatogenic Dysfunction and Affects Cell Proliferation, Apoptosis, and Migration", Reproductive Sciences—7 pages (Dec. 30, 2015).
Ciavardelli et al., "Alterations of brain and cerebellar proteomes linked to Aβ and tau pathology in a female triple-transgenic murine model of Alzheimer's disease", Cell Death and Disease—11 pages (Oct. 28, 2010).
Xu et al., "The diagnostic value and functional roles of phosphoglycerate mutase 1 in glioma", Oncology Reports, vol. 36, No. 4—9 pages (Aug. 25, 2016).
Mishra et al., "Translocation of HIV TAT peptide and analogues induced by multiplexed membrane and cytoskeletal interactions", PNAS, vol. 108, No. 41—6 pages (Oct. 11, 2011).

(Continued)

*Primary Examiner* — Amber D Steele
(74) *Attorney, Agent, or Firm* — Knobbe Martens Olson & Bear LLP

(57) ABSTRACT

A protein transduction domain and a fusion compound, which are more efficient, are proposed. As a result of selecting and testing a number of candidate peptides, the present inventors found that a GK1 peptide comprising 18 amino acids and a modified sequence obtained by replacing, adding, or deleting some sequences are bonded to high-molecular-weight materials such as proteins based on the basic sequence of the peptide, thus enabling the high-molecular-weight materials to smoothly penetrate into living bodies, for example, cells, tissues, or blood. A fusion compound, oligonucleotide, or vector using the same may be applied as a pharmaceutical composition for preventing or treating diseases.

9 Claims, 8 Drawing Sheets

Specification includes a Sequence Listing.

(56) References Cited

OTHER PUBLICATIONS

Mao et al., "Influence of structure and properties of colloidal biomaterials on cellular uptake and cell functions", Biomaterials Science, vol. 1—16 pages (Jul. 15, 2013).
Stewart et al., "Cell-penetrating peptides as delivery vehicles for biology and medicine", Organic & Biomolecular Chemistry, vol. 6, No. 13—14 pages (Apr. 15, 2008).
Beevers et al., "Helical membrane peptides to modulate cell function", Chemical Society Reviews, vol. 6—12 pages (Mar. 10, 2010).
Galdiero et al., "Peptide-Lipid Interactions: Experiments and Applications", International Journal of Molecular Sciences, vol. 14—32 pages (Sep. 12, 2013).
Sebbage, "Cell-penetrating peptides and their therapeutic applications", Bioscience Horizons—9 pages (Feb. 17, 2009).
Munyendo et al., "Cell Penetrating Peptides in the Delivery of Biopharmaceuticals", Biomolecules, vol. 2—16 pages (Mar. 30, 2012).

A

B

PROTEIN TRANSDUCTION DOMAIN, FUSION COMPOUND CONTAINING THE SAME, AND PHARMACEUTICAL COMPOSITION CONTAINING THE FUSION COMPOUND

RELATED APPLICATION

The present application is being filed along with a Sequence Listing in electronic format. The Sequence Listing is provided as a file entitled 569318041.TXT, created and last modified on Jan. 10, 2023, which is 16.5 Kb in size. The information in the electronic format of the Sequence Listing is incorporated herein by reference in its entirety.

REFERENCE TO SEQUENCE LISTING

The present application is being filed along with a Sequence Listing in electronic format. The Sequence Listing is provided as a file entitled 34468813_1.TXT, created and last modified on Feb. 23, 2021, which is 16.5 Kb in size. The information in the electronic format of the Sequence Listing is incorporated herein by reference in its entirety.

BACKGROUND OF THE DISCLOSURE

1. Field of the Disclosure

The present disclosure relates to a protein transduction domain that comprises a peptide of the 18 amino acids AANDLAEGLAELADTVGV (SEQ ID NO: 1) or a peptide obtained by deleting, replacing, or adding some amino acids thereof. Further, the present disclosure relates to a fusion compound in which the protein transduction domain is bonded to cargo molecules, and to a pharmaceutical composition including the fusion compound.

2. Description of the Related Technology

A protein transduction domain (PTD) or cell-penetrating peptide (CPP) is a delivery system that fuses a peptide comprising approximately 5 to 30 amino acids with high-molecular-weight materials such as proteins or nucleic acids, thus easily delivers the fused substances into living bodies, for example, mammalian cells, tissues, or blood. Although the specific mechanism has not yet been accurately identified, a protein delivery technology has been used to deliver proteins into cells or tissues for in-vitro or in-vivo treatment, and various protein transduction domains are known. The protein transduction domain is conveniently fused with biological cargo molecules for transduction and does not affect the structure or function of the cargo molecules, and thus the fused compound is stable. Accordingly, the protein transduction domain is used in medicines and cosmetics.

The disclosure of this section is to provide background information relating to the invention. Applicant does not admit that any information contained in this section constitutes prior art.

SUMMARY OF THE DISCLOSURE

Therefore, an aspect of the present disclosure provides a novel protein transduction domain that is more efficient and safer than a conventional protein transduction domain.

Another aspect of the present disclosure is to provide a fusion compound bonded to the novel protein transduction domain.

Another aspect of the present disclosure is to provide a pharmaceutical composition including the fusion compound.

Another aspect of the present disclosure is to provide a cosmetic composition including the fusion compound.

Another aspect of the present disclosure is to provide a method for smoothly transporting useful high-molecular-weight materials such as proteins or nucleic acids into cells or tissues.

As a result of selecting and testing a number of candidate peptides, the present inventors found that a peptide comprising the 18 amino acids AANDLAEGLAELADTVGV (SEQ ID NO: 1) (hereinafter, referred to as "GK1" in the present disclosure) or a peptide obtained by deleting, replacing, or adding some amino acids thereof enables high-molecular-weight materials such as proteins to smoothly transport into living bodies, for example, cells, tissues, or blood.

Definitions of main terms used in the description and claims of the present disclosure are as follows.

"Cargo molecules" are molecules other than a protein transduction domain or fragments thereof, which cannot enter target cells naturally or cannot enter target cells at the useful rate naturally. "Cargo molecules" refer to the target molecules before fusion with the protein transduction domain or the target molecule part of the protein transduction domain-target molecule complex. The cargo molecules refer to any one selected from among proteins, peptides, amino acids, nucleic acids, carbohydrates, lipids, and a mixture of one or more thereof.

"Target proteins" as a concept included in the "cargo molecules" are molecules other than a protein transduction domain or fragments thereof, which cannot enter target cells naturally or cannot enter target cells at the useful rate naturally. The target proteins refer to the target protein molecules before fusion with the protein transduction domain or the target protein part of the protein transduction domain-target protein complex. The target proteins include polypeptide, protein, or peptide. Examples of the target proteins may include PGAM1 (phosphoglycerate mutase 1), BLVRA (biliverdin reductase A), superoxide dismutase, an epithelial cell growth factor, a fibroblast growth factor, catalase, and FK506BP (FK506-binding protein). However, it is obvious to a person skilled in the art that the above examples are only partial illustrations of the target protein, and the target protein is not limited thereto.

"Fusion proteins" include a transduction domain and one or more target protein parts, and the term refers to a complex formed by genetic fusion or chemical bonding between the transduction domain and the target protein.

Further, "genetic fusion" refers to a linear linkage obtained by covalent bonding through the genetic expression of a DNA sequence encoding a protein. Further, "target cells" means cells to which a target protein is delivered by a protein transduction domain. The target cells refer to intracorporeal or extracorporeal cells. In other words, "target cells" is meant to include intracorporeal cells, that is, cells that make up organs or tissues of living animal or human, or microorganisms found in living animals or humans. Further, "target cells" is meant to include extracorporeal cells, that is, cultured animal cells, cultured human cells, or cultured microorganisms.

"Protein transduction domain" in the present disclosure refers to a peptide that forms a covalent bond with highmolecular-weight organic compounds, for example, oligonucleotides, peptides, proteins, oligosaccharides, or polysaccharides, thereby introducing the organic compounds into cells or tissues without requiring separate receptors, carriers, or energy.

Further, in this specification, with respect to the "transduction" of proteins, peptides, or organic compounds into cells or tissues, the terms "penetrating" and "transporting" may be used interchangeably therewith.

The present disclosure relates to a protein transduction domain which is any one selected from (A) to (C) below, includes 18 to 29 amino acids, and is chemically bonded to cargo molecules to thus transport the cargo molecules into mammalian cells or tissues.

(A)($X_1X_2X_3$)-DLAEGLAELADT-($X_4X_5X_6$) (SEQ ID NO:49),
wherein $X_1$ is A or R, $X_2$ is A or R, $X_3$ is N or R, $X_4$ is V or R, $X_5$ is G or R, and X6 is V or R,
(B) ($R_7$)-AANDLAEGLAELADTVGV (SEQ ID NO: 1) or AANDLAEGLAELADTVGV (SEQ ID NO: 1)-($R_7$),
wherein $R_7$ is R, RR, or RRR), and
(C) ($R_8$)-AANDLAEGLAELADTVGV (SEQ ID NO: 1) or AANDLAEGLAELADTVGV (SEQ ID NO: 1)-($R_8$),
wherein $R_8$ is RKKRRQRRR (SEQ ID NO: 54), KETWWET (SEQ ID NO: 55), or EWSQPKKKRKV (SEQ ID NO: 56).

Further, in the present disclosure, the protein transduction domain is any one selected from SEQ ID NO: 1 to SEQ ID NO: 23. The protein transduction domain of the present disclosure is not limited to SEQ ID NO: 1 to SEQ ID NO: 23, but it should be noted that representative peptides are listed in Table 1 for convenience of experimentation.

"Protein transduction domain" according to the present disclosure is interpreted to mean including variants, in which one or more amino-acid residues are conservatively substituted at specific amino-acid residue positions, or fragments thereof including eighteen or more amino acids among fragments in which one to three amino acids are deleted at the N-terminus and/or C-terminus thereof.

In the present specification, "conservative substitution" refers to modification of a protein transduction domain, including substitution of one or more amino acids with amino acids that do not cause loss of biological or biochemical functions of the corresponding protein transduction domain and have biochemical properties similar thereto.

In the present specification, "conservative substitution of amino acids" is a substitution of amino acid residues with amino acid residues having similar side chains. Classes of amino acid residues having similar side chains can be defined. Examples thereof include amino acids having basic side chains (for example, lysine, arginine, and histidine), amino acids having acidic side chains (for example, aspartic acid and glutamic acid), amino acids having uncharged polar side chains (for example, glycine, asparagine, glutamine, serine, threonine, tyrosine, and cysteine), amino acids having non-polar side chains (for example, alanine, valine, leucine, isoleucine, proline, phenylalanine, methionine, and tryptophan), amino acids having beta-branched side chains (for example, threonine, valine, and isoleucine), and amino acids having aromatic side chains (for example, tyrosine, phenylalanine, tryptophan, and histidine).

It is expected that the activity of the protein transduction domain of the present disclosure or fragments thereof will be maintained even when conservative substitution of amino acids is performed.

Further, the protein transduction domain variant according to the present disclosure is interpreted to have substantially the same function and/or effect as the protein transduction domain according to the present disclosure, and has the meaning of including protein transduction domain variants or fragments thereof having an amino acid sequence homology of 80% or 85% or more, in an embodiment, 90% or more, and in another embodiment, 95% or more.

Further, in the present disclosure, the cargo molecules are selected from among proteins, peptides, amino acids, nucleic acids, carbohydrates, lipids, and a mixture of one or more thereof.

Further, in the present disclosure, the cargo molecules are selected from among nanoparticles, microparticles, liposomes, and micelles.

Further, in the present disclosure, the chemical bonding of the protein transduction domain and the cargo molecules is covalent bonding or non-covalent bonding. The chemical bonding may be covalent bonding or non-covalent bonding. Examples of the non-covalent bonding may include ionic bonding, bonding by electrostatic attraction, or bonding by hydrophobic interaction. Further, the material capable of being bonded to the protein transduction domain by the ionic bonding or electrostatic attraction may be a material having one or more charges, such as DNA or RNA.

Further, the present disclosure relates to a fusion compound that easily penetrates into cells or tissues. The fusion compound includes a protein transduction domain which is any one selected from (A) to (C) as described above and is bonded to cargo molecules for preventing or treating diseases to transport the cargo molecules into cells or tissues.

Further, the present disclosure relates to a fusion compound that easily penetrates into cells or tissues, in which the protein transduction domain is any one selected from SEQ ID NO: 1 to SEQ ID NO: 23. The protein transduction domain of the present disclosure is not limited to SEQ ID NO: 1 to SEQ ID NO: 23, but it should be noted that representative peptides are listed in Table 1 for convenience of experimentation.

Further, the present disclosure relates to a fusion compound in which the cargo molecules are selected from among proteins, peptides, amino acids, nucleic acids, carbohydrates, lipids, and a mixture of one or more thereof.

Further, the present disclosure relates to a fusion compound in which the cargo molecules are selected from among nanoparticles, microparticles, liposomes, and micelles.

Further, the present disclosure relates to a pharmaceutical composition for preventing or treating diseases including the above-described fusion compound, which easily penetrates into cells or tissues.

Further, the present disclosure relates to a cosmetic composition including the above-described fusion compound, which is easily transduced into cells or tissues. The cosmetic composition of the present disclosure may include basic cosmetics, such as lotions, creams, essences, oil-in-water- or water-in-oil-type of emulsions, and ointments, as well as color cosmetics such as foundation, lipstick, and eye shadow.

Further, the present disclosure relates to a recombinant polynucleotide encoding a fusion compound that easily penetrates into cells or tissues, in which an oligonucleotide sequence encoding the protein transduction domain is bonded to a cDNA sequence encoding cargo molecules for preventing or treating diseases so that the protein transduction domain is chemically bonded to the cargo molecules for preventing or treating diseases.

Further, the present disclosure relates to a recombinant polynucleotide encoding a fusion compound that easily penetrates into cells or tissues, in which the oligonucleotide sequence encoding the protein transduction domain is any one selected from SEQ ID NO: 24 to SEQ ID NO: 46. The oligonucleotide encoding the protein transduction domain of the present disclosure is not limited to SEQ ID NO: 24 to SEQ ID NO: 46, but it should be noted that representative oligonucleotides are illustrated in Table 2 for convenience of experimentation.

Further, the present disclosure relates to a pharmaceutical composition for preventing or treating diseases, which includes the recombinant polynucleotide encoding a fusion compound that easily penetrates into cells or tissues.

Further, the present disclosure relates to a method for treating disease in a subject, said method consisting of administering to said subject a therapeutically effective amount of the fusion compound penetrating into mammalian cell or tissues. The fusion protein of the present disclosure invention can be administered to a subject suffering from such a disease or suspected of a disease to prevent or treat a disease caused by a lack of a cargo protein.

Further, the present disclosure relates to a fusion-compound expression vector including the recombinant polynucleotide encoding a fusion compound that easily penetrates into cells or tissues.

Further, the present disclosure relates to a pharmaceutical composition for preventing or treating diseases, which includes the fusion-compound expression vector.

A pharmaceutical composition that includes the fusion compound of the present disclosure, an oligonucleotide encoding the same, or a vector containing the oligonucleotide as an active ingredient may be blended with a typical carrier acceptable for use in the pharmaceutical field, and may be formulated in various forms, such as external skin preparations, oral types, spray types, patches, or injection types, according to a typical method. For example, the oral compositions include tablets and gelatin capsules. The oral compositions include, in addition to the active ingredients, a diluent (e.g.: lactose, dextrose, sucrose, mannitol, sorbitol, cellulose, and/or glycine), and a lubricating agent (e.g.: silica, talc, stearic acid and magnesium or calcium salts thereof, and/or polyethylene glycol). In embodiments, tablet includes a binding agent (e.g.: magnesium aluminum silicate, starch paste, gelatin, methylcellulose, sodium carboxymethylcellulose, and/or polyvinyl pyrrolidone), and includes a disintegrant (e.g.: starch, agar, alginic acid or sodium salts thereof), a boiling mixture and/or an absorbent, a colorant, a flavoring agent, and a sweetening agent, in some cases. In embodiments, the composition for injection is an isotonic aqueous solution or suspension. The above-described composition is sterilized and/or contains an adjuvant (e.g.: a preservative, a stabilizer, a wetting- or emulsification-promoting agent, and salts and/or buffers for controlling osmotic pressure). Further, other materials that are therapeutically useful may be contained therein.

The pharmaceutical preparation prepared as described above may be orally administered, may be parenterally administered, that is, intravenously, subcutaneously, or intraperitoneally administered, or may be topically applied depending on the purpose thereof. With respect to the dose thereof, the pharmaceutical preparation may be administered by dividing the daily dose of 0.0001 to 100 mg/kg into one to several administrations. The dosage level for a specific patient may depend on the patient's weight, age, sex, and health status, administration time, administration method, excretion rate, and severity of disease.

In one embodiment in the present disclosure provides a method for treating disease in a subject, said method consisting of administering to said subject a therapeutically effective amount of the fusion compound penetrating into mammalian cell or tissues. In another embodiment in the present disclosure provides a method for treating disease in a subject, said method comprising administering to said subject a therapeutically effective amount of the fusion compound penetrating into mammalian cell or tissues. The fusion protein according to embodiments of the present invention can be administered to a subject suffering from such a disease or suspected of a disease to prevent or treat a disease caused by a lack of a cargo protein.

The novel protein transduction domain of the present disclosure may be bonded to cargo molecules such as proteins to form a fusion compound, thereby easily penetrating into cells or tissues.

Further, the fusion compound, in which the novel protein transduction domain of the present disclosure is bonded to cargo molecules, exhibits activity in cells or tissues. Accordingly, the fusion compound, the oligonucleotide encoding the same, or a vector including the oligonucleotide may be used as a pharmaceutical composition for preventing or treating diseases.

Further, it is possible to enable cargo molecules such as proteins to easily penetrate into cells or tissues using the novel protein transduction domain of the present disclosure.

BRIEF DESCRIPTION OF THE DRAWINGS

The above and other aspects, features and advantages of the present disclosure will be more clearly understood from the following detailed description taken in conjunction with the accompanying drawings, in which.

The median number of the fusion protein is the name of the protein transduction domain shown in Table 1.

Figure 6:
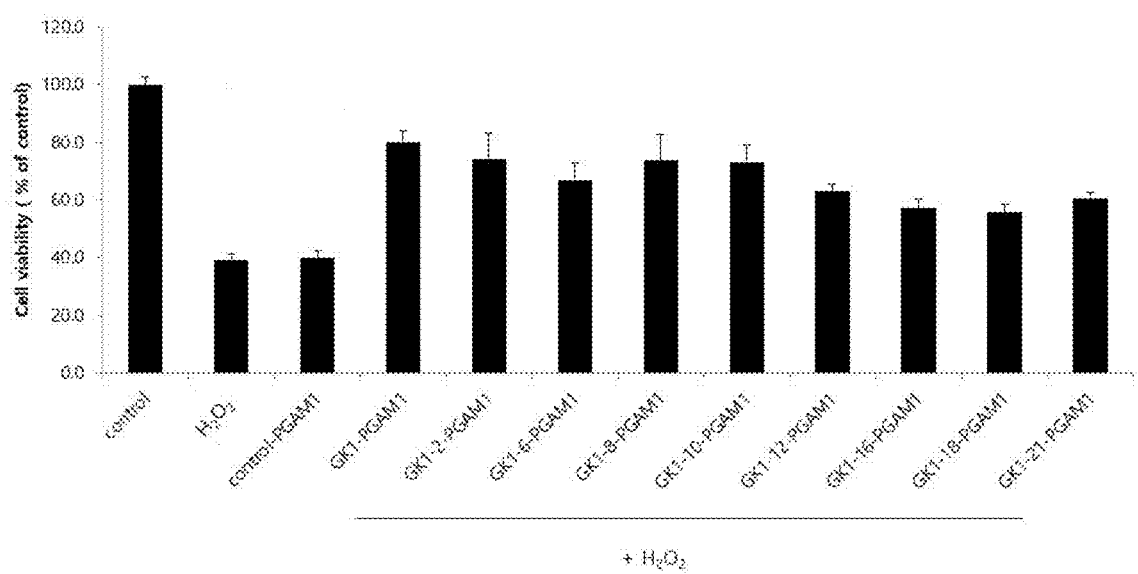

FIG. 6 shows the results obtained by testing the protective effect of cell-transduced PGAM1 fusion proteins against oxidative stress. Cells were treated with GK1-PGAM1 fusion proteins and a control PGAM1 protein at a concentration of 5 μM for 1 hour, and were then treated with 100 μM $H_2O_2$ for 1 hour. Then, cell viability was evaluated using an MTT analysis method. The median number of the fusion protein is the number of the protein transduction domain shown in Table 1.

DESCRIPTION OF EMBODIMENTS

Hereinafter, the configuration of the present disclosure will be described in more detail with reference to specific Examples. However, it is apparent to those of ordinary skill in the art that the scope of the present disclosure is not limited only to the description of the Examples.

The numerous protein transduction domains may be divided into three categories. The first is an amphiphilic peptide, and examples thereof may include a Pep-1 peptide. The Pep-1 peptide consists of 21 amino acids (KETWWETWWTEWSQPKKKRKV; SEQ ID NO: 57) and has three domains, namely a hydrophobic domain, a spacer, and a hydrophilic domain. The second is a cationic peptide, and examples thereof may include a HIV-Tat peptide (Hereinafter, "Tat" or "Tat peptide"), oligolysine, oligoarginine, and oligo (lysine+arginine). The sequence of the cell-transducing Tat peptide includes RKKRRQRRR (SEQ ID NO: 54), and the peptide has been used in the study of various proteins for treatment. The third is a hydrophobic peptide.

A bonding between a protein transduction domain and a biological cargo molecule (for example, nucleic acids, proteins, peptides, small molecules, cytotoxic drugs etc.) may be accomplished using various methods such as ionic bond and electrostatic bond, in addition to covalent bond.

The protein transduction domain has advantages of exhibiting lower toxicity and less frequent immunorejection than other delivery substances such as liposomes or polymers. However, few protein transduction domains are used in clinical practice.

<Method>
1. Cell Culture

NSC34 cell line, which is a mouse-motoneuron-like hybrid cell line, was distributed from College of Natural Sciences of Hallym University. The cell culture solution was prepared by adding 10% fetal bovine serum (FBS) and an antibiotic solution (100 units/ml penicillin, 100 μg/ml streptomycin) to a DMEM medium. The NSC34 cell line was cultured using the above cell culture solution at 37° C. and 95% humidity under the condition in which 5% $CO_2$ was maintained. When the cell reaches 70 to 80% confluent, treatment with trypsin-EDTA was performed to accomplish subculture.

2. Construction of Recombinant GK1

Annealing was performed at 37° C. for 2 hours using the following oligonucleotides.

```
Sense oligonucleotide (SEQ ID NO: 47):
tatggctgcgaatgatcttgcggaaggtctggcggaactcgcggatacgg taggcgtaca,
```

```
Anti-sense oligonucleotide (SEQ ID NO: 48):
tatgtacgcctaccgtatccgcgagttccgccagaccttccgcaagatca ttcgcagcca.
```

Thereafter, the NdeI site of a pET-15b vector was cut, and the GK1-coding oligonucleotide pairs prepared in the above were connected. Transformation of the *Escherichia coli* strain Top 10 with the recombinant GK1 was performed. The DNA separated from the transformed cell was amplified through PCR using the following primers.

Forward primer: T7, reverse primer: T7 terminator.

The BamHI and XhoI sites of the GK1 vector were cut to connect PGAM1 (phosphoglycerate mutase 1), BLVRA (biliverdin reductase A) or CNRIP1 (Cannabinoid Receptor Interacting Protein 1) gene.

3. Expression and Purification of Recombinant GK1

Transformation of *Escherichia coli* strain BL21 with the recombinant GK1 plasmid was performed. After the transformed cell was cultured in 100 ml LB medium containing 100 μg/ml ampicillin at 37° C. and 180 rpm for 6 hours, 0.5 mM IPTG (isopropyl-β-D-thiogalactoside) was added thereto, and then culture was performed at 37° C. and 120 rpm for 16 hours. The recovered cells were subjected to ultrasonic treatment and centrifuged to isolate only a supernatant, followed by purification using an $Ni^{2+}$-nitrilotriacetic acid Sepharose affinity chromatography column. A protein concentration was normalized with bovine serum albumin (BSA) and quantified using a protein quantitative assay kit.

4. Transduction of GK1 Fusion Protein into NSC34 Cells

The NSC34 cell was dispensed on a 60 mm plate and cultured under conditions of 37° C., 95% humidity, and 5% $CO_2$. In order to examine the cell penetration capability of GK1, Pep-1-PGAM1 fusion protein, Tat-PGAM1 fusion protein, and GK1-PGAM1 fusion protein at the same concentration (5 μM) were used in treatment for 20 minutes, respectively. Further, in order to confirm that the cell penetration capability of the protein transduction domain GK1 is shown in arbitrary protein, another protein at the same concentration, namely, a GK1-BLVRA fusion protein, was used in treatment for 20 minutes. The cultured cells were rinsed with PBS (phosphate-buffered saline). In order to extract proteins, a RIPA lysis buffer was added thereto and centrifuged (4° C., 12,000 rpm, and 10 min), thereby performing protein quantification with respect to the supernatant.

In order to compare the cell transduction efficiency, a Pep-1-PGAM1 fusion protein and a Tat-PGAM1 fusion protein that are fusion proteins using Pep-1 peptide and Tat peptide, were prepared according to a method similar to the method described above (Kim W. et al., Neurochemistry International, 10 Dec. 2019, 133:104631). Thereafter, the Pep-1-PGAM1 fusion protein and the Tat-PGAM1 fusion protein were transduced into NSC34 cell according to the method as described above.

5. Western Blotting Analysis

50 μg of the fusion protein or the control protein was mixed with a 5× sample buffer and then boiled for 2 minutes to prepare a protein sample, followed by separation according to molecular weight using 15% mini gel SDS-PAGE (sodium dodecyl sulfate polyacrylamide gel electrophoresis). After the electrophoresis was finished, the resultant was transferred to a nitrocellulose membrane, and blocking of the membrane was carried out using TBS-T (pH 7.5, 25 mM Tris-Cl, 150 mM NaCl, and 0.1% Tween 20) containing 5% skim milk at room temperature for 1 hour. In order to measure the expression of the protein, a primary antibody (anti-histidine probe) was diluted in the TBS-T at a ratio of 1:1,000, reacted at room temperature for 1 hour, and then washed with the TBS-T. A HRP (horseradish peroxidase)-conjugated-anti-rabbit IgG as a secondary antibody was diluted in TBS-T at a ratio of 1:10,000 to be reacted at room temperature for 1 hour. After washing with the TBS-T, the expression level of each protein was confirmed using a detection reagent.

6. Fluorescence Microscope Analysis

Each glass cover slip was placed on a 24-well plate, and cells were dispensed thereon and cultured for 24 hours. After 5 μM of the Pep-1-PGAM1 fusion protein, Tat-PGAM1 fusion protein, GK1-PGAM1 fusion protein, or GK1-BLVRA fusion protein was transduced into an NSC34 cell for 2 hours, the culture medium was removed, and rinsing was repeated with PBS three times. After 4% para-formaldehyde was added to each well and the cells were fixed for 5 minutes, PBS was added thereto, and washing was repeated three times for a short time. After blocking and penetration in PBS (PBS-BT) containing 3% BSA and 0.1% Triton X-100 at room temperature for 40 minutes, washing with PBS-BT was repeated three times. A His-probe primary antibody was diluted at a ratio of 1:2,000 and cultured at room temperature for 1 hour. A secondary antibody (Alexa Fluor 488) was diluted to a ratio of 1:10,000, reacted for 1 hour in dark, and washed with the PBS-BT three times for 5 minutes. The glass cover slip was separated from the well to remove moisture from the edge thereof, and was lifted. A fluorescence microscope was used for observation, and fluorescence emission was confirmed using an image analyzer.

<Result>

Result 1: Schematic Diagram and Purification of GK1 Fusion Protein

Figure 1A:
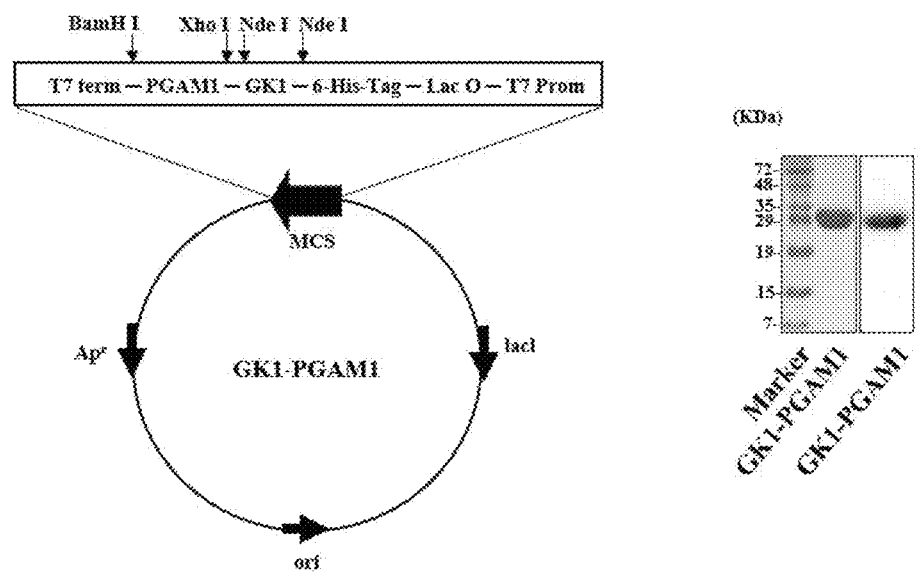
FIGS. 1A and 1B show the construction of a GK1 expression vector on a pET-15b vector. A synthetic GK1 oligomer was cloned at the NdeI site, and human PGAM1 (phosphoglycerate mutase 1) cDNA or human BLVRA (biliverdin reductase A) cDNA was cloned at the XhoI and BamHI sites of pET-15b.
Figure 1B:
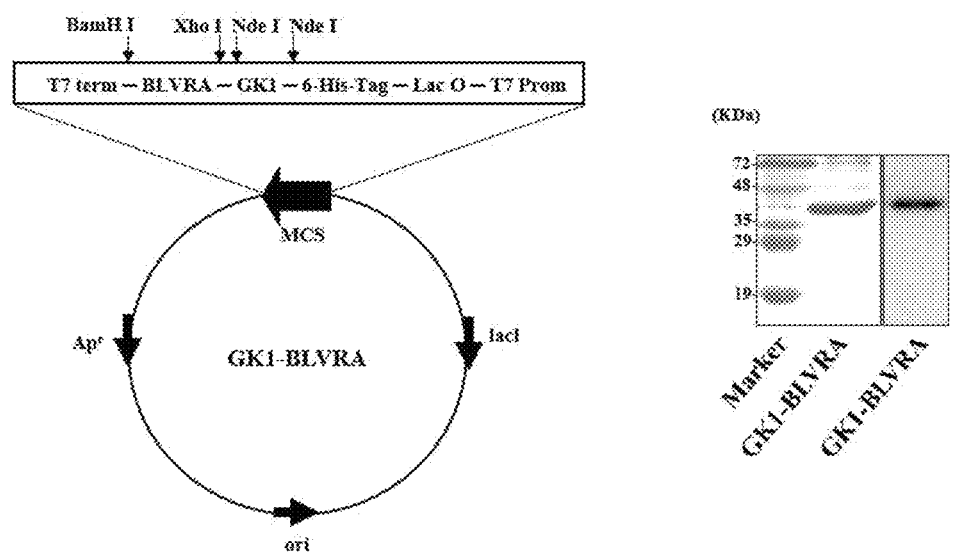

In order to express the protein transduction domain, cloning of a GK1 oligonucleotide (gct gcg aat gat ctt gcg aaa ggt ctg gcg gaa ctc gcg gat acg gta ggc gta; SEQ ID NO: 24) was performed at an NdeI site of a pET-15b plasmid. In order to confirm the cell penetration efficiency of the protein transduction domain GK1, cloning of PGAM1 (phosphoglycerate mutase 1) cDNA or BLVRA (biliverdin Reductase A) cDNA was performed at XhoI and BamHI sites of the pET-15b plasmid containing GK1 oligonucleotide. In the case of a control vector, cloning of the PGAM1 protein or the BLVRA protein was performed at the pET-15b plasmid not containing the GK1 oligonucleotide. After expression of the fusion protein or the protein, purification was performed using an $Ni^{2+}$-nitrilotriacetic acid Sepharose affinity chromatography column, and was confirmed using SDS-PAGE [FIGS. 1A and 1B].

Result 2: Transduction of GK1 Fusion Protein into Cell

Figure 2:
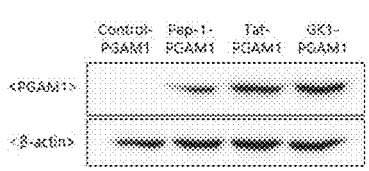
FIG. 2 shows results of western blotting analysis. A of FIG. 2 shows the result of western blotting analysis of the level of cell-transduced proteins after cells are treated with a Pep-1-PGAM1 fusion protein, a GK1-PGAM1 fusion protein, or a Tat-PGAM1 fusion protein for 1 hour. B of FIG. 2 shows the results of western blotting of cells treated with a GK1-PGAM1 fusion protein or a GK1-BLVRA fusion protein.
Figure 2:
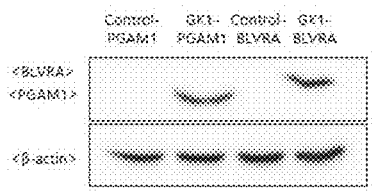
Figure 2:
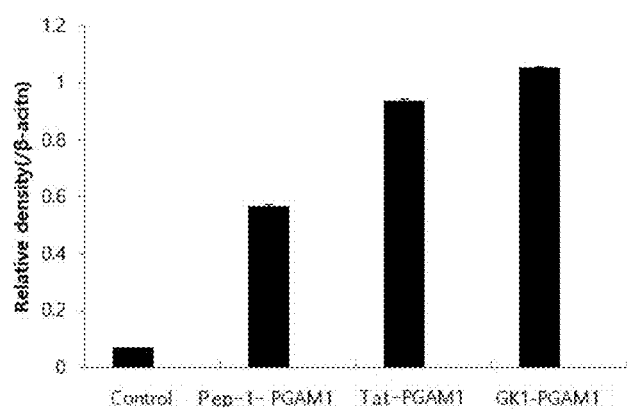

In order to examine the cell transduction efficiency of GK1, the Pep-1-PGAM1 fusion protein, the GK1-PGAM1 fusion protein, or the Tat-PGAM1 fusion protein at the same concentration (5 μM) was used to treat an NSC34 cell for 1 hour. Then, the cell transduction level was analyzed by western blotting. The level of intracellular fusion protein was highest in the case of the GK1-PGAM1 fusion protein. In comparison with the GK1-PGAM1 fusion protein, the Tat-PGAM1 fusion protein showed a cell transduction level of about 89%, and the Pep-1-PGAM1 fusion protein showed a cell transduction level of about 50% [A of FIG. 2]. The control PGAM1 protein did not penetrate into the cells.

In order to prove that the cell-penetrating domain GK1 was fused with an arbitrary protein to penetrate the cell, the GK1-PGAM1 fusion protein and the GK1-BLVRA fusion protein, prepared by fusing the protein transducing domain GK1 with the two types of proteins PGAM1 and BLVRA respectively were used at the same concentration (5 μM) to treat the cell for 1 hour. Although there is a difference in cell transduction efficiency depending on the protein type, the two types of proteins smoothly penetrated into the NSC34 cells [B of FIG. 2].

Figure 3A:
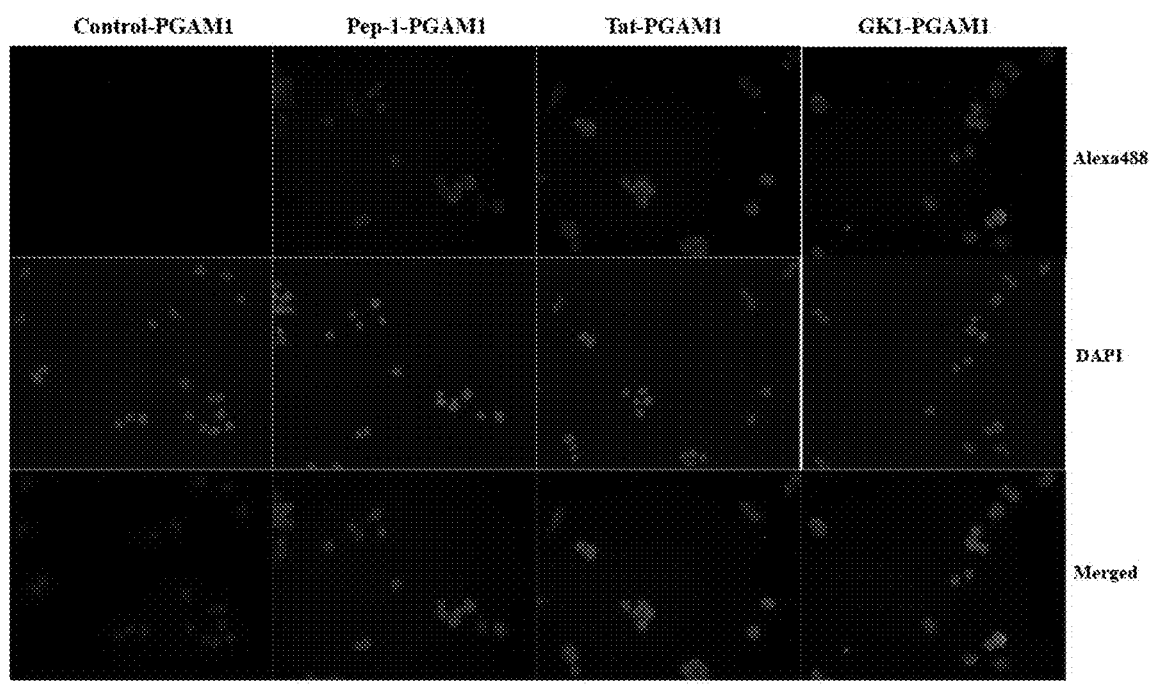
FIG. 3A shows the intracellular locations and levels of a cell-transduced control PGAM1 protein, a Pep-1-PGAM1 fusion protein, a GK1-PGAM1 fusion protein, and a Tat-PGAM1 fusion protein, which are photographed using a confocal fluorescence microscope.

In order to examine the location of the Pep-1-PGAM1 fusion protein, GK1-PGAM1 fusion protein, or Tat-PGAM1 fusion protein transduced into the cells, the cells into which each fusion protein penetrated were subjected to immunostaining using DAPI and Alexa Fluor 488-conjugated secondary antibodies. A control PGAM1 protein was not observed in the NSC34 cell. Unlike this, the Pep-1-PGAM1 fusion protein, the GK1-PGAM1 fusion protein, and the Tat-PGAM1 fusion protein were detected mainly in the cytoplasm using a fluorescence microscope, and were also detected in the nucleus [FIG. 3A]. Further, in the case of the GK1-PGAM1 fusion protein, a fluorescence signal having a higher intensity was observed compared to the Pep-1-PGAM1 fusion protein and the Tat-PGAM1 fusion protein. This implies that the cell transduction efficiency of the GK1-PGAM1 fusion protein is the highest.

Figure 3B:
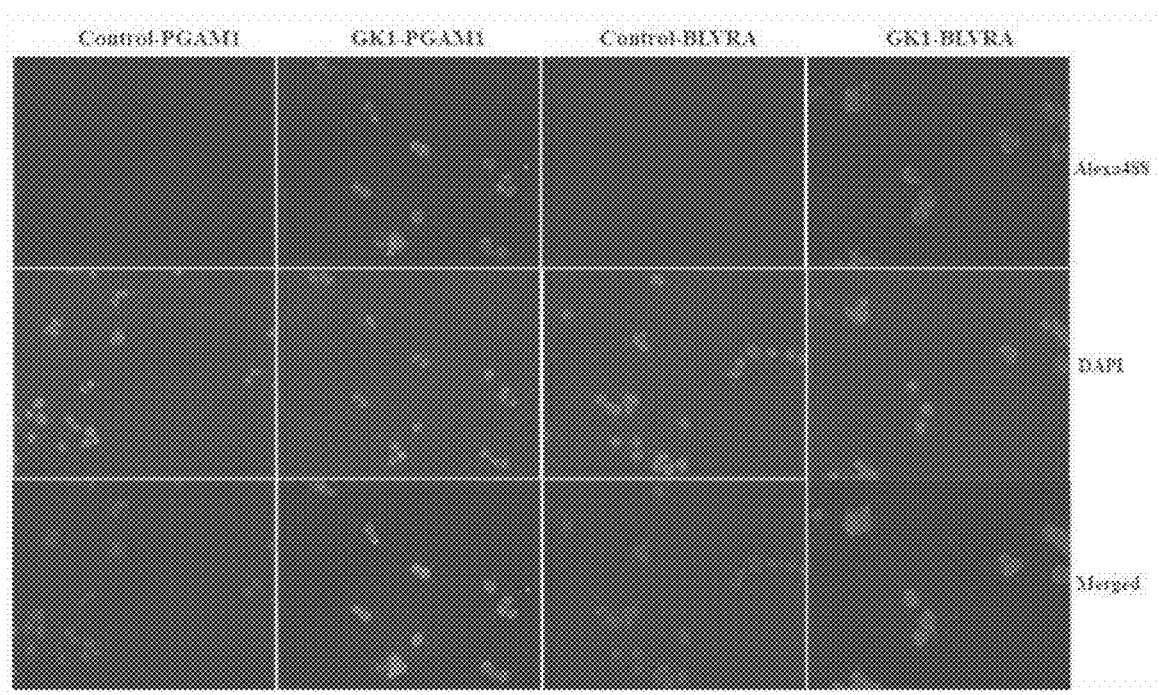
FIG. 3B shows the intracellular locations and levels of a cell-transduced control PGAM1 protein, a GK1-PGAM1 fusion protein, a control BLVRA protein, and a GK1-BLVRA fusion protein, which are photographed using a confocal fluorescence microscope.
Figure 4:
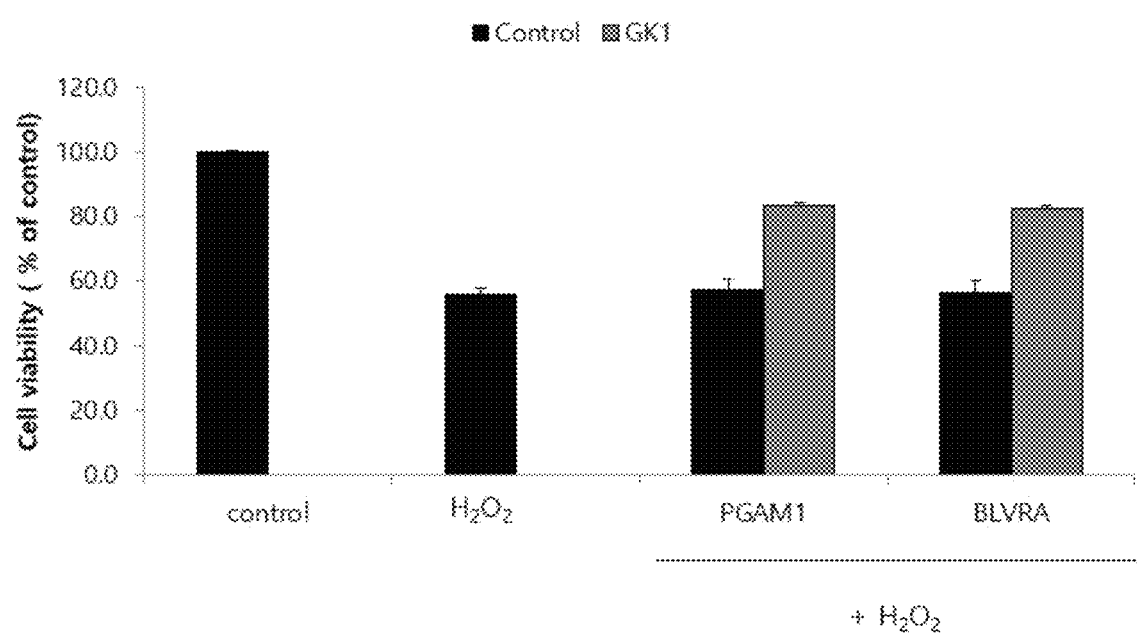
FIG. 4 is a graph showing the protective effect of each protein against oxidative stress. Cells were pre-treated with each of a control PGAM1 protein, a GK1-PGAM1 fusion protein, a control BLVRA protein, and a GK1-BLVRA fusion protein at a concentration of 5 μM for 1 hour, and were then treated with 100 μM $H_2O_2$ for 1 hour. Then, cell viability was evaluated using an MTT analysis method.

Further, the intracellular location of the GK1 fused with an arbitrary protein to penetrate into a cell was examined using the above-described method. The GK1-PGAM1 fusion protein and the GK1-BLVRA fusion protein were detected mainly in the cytoplasm, and were also detected in the nucleus [FIGS. 3A and 3B].

Result 3: Effect of GK1 Fusion Protein Against Oxidative Stress

It was examined whether the GK1 fusion protein transducing into cells had a protective effect against oxidative stress. Treatment was performed with a GK1-PGAM1 fusion protein, a GK1-CNRIP1 fusion protein, a control PGAM1 protein, and a control CNRIP1 protein at a constant concentration (5 μM) for 1 hour, followed by treatment with 100 μM $H_2O_2$ for 1 hour. Thereafter, cell viability was evaluated using an MTT analysis method [FIGS. 5A and 5B]. The viability of the cell treated with $H_2O_2$ was reduced by about 57% compared to the control cell. The viability of the cell pre-treated with GK1-PGAM1 fusion protein or GK1-BLVRA fusion protein was increased by about 83%. In comparison, the control PGAM1 protein and the control CNRIP1 protein had no protective effect against cell death caused by $H_2O_2$.

Result 4: Transduction of Fusion Protein Using the GK1 Protein Transduction Domain into Cells and Effect Thereof Against Oxidative Stress A GK1 peptide sequence (AANDLAEGLAELADTVGV; SEQ ID NO: 1) or a GK1 derivative peptide in which one or more peptides are substituted into or added to a part of the sequence, sequences in which partial consecutive sequence of the GK1 peptide and sequence of Tat peptide or partial consecutive sequence thereof are bonded, and sequences in which partial consecutive sequence of the GK1 peptide and native or partial consecutive sequence of the Tat peptide, and native or partial consecutive sequence of the Pep-1 peptide are bonded are shown in Table 1. It should be noted that the sequences listed in Table 1 are just some examples of the protein transduction domain claimed in the present disclosure, and the protein transduction domain of the present disclosure is not limited to the sequences listed in Table 1.

Figure 5A:
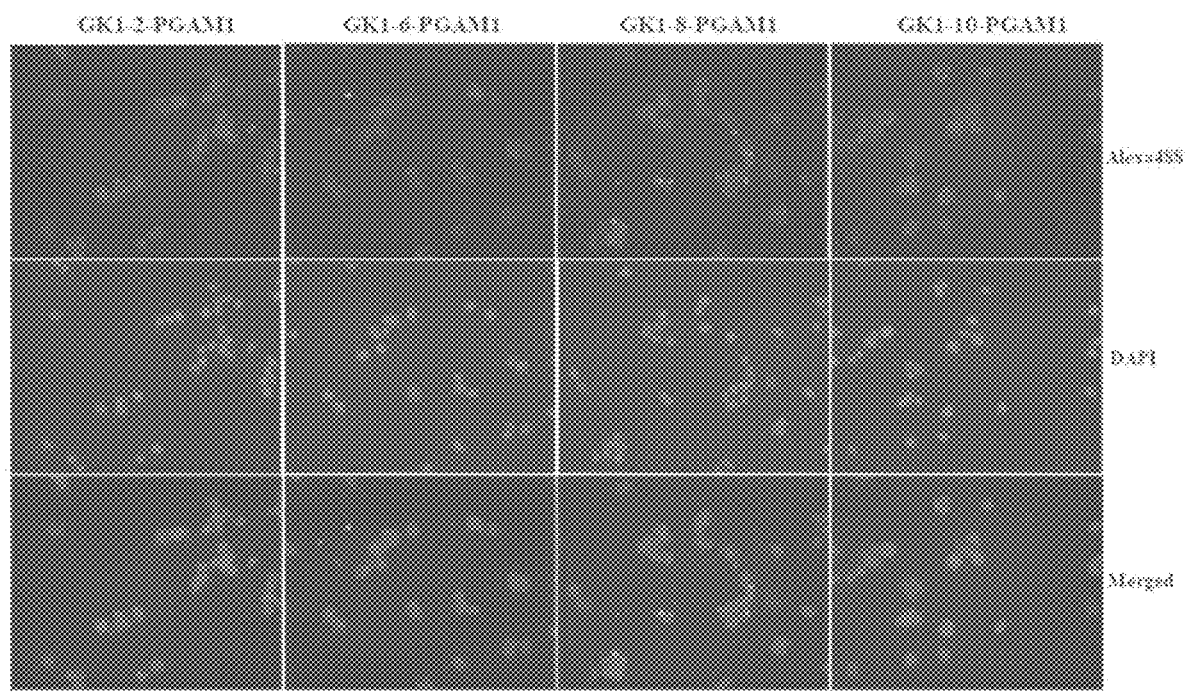
FIG. 5A and FIG. 5B show the intracellular location and level of a cell-transduced PGAM1 fusion protein, which are photographed using a confocal fluorescence microscope.
Figure 5B:
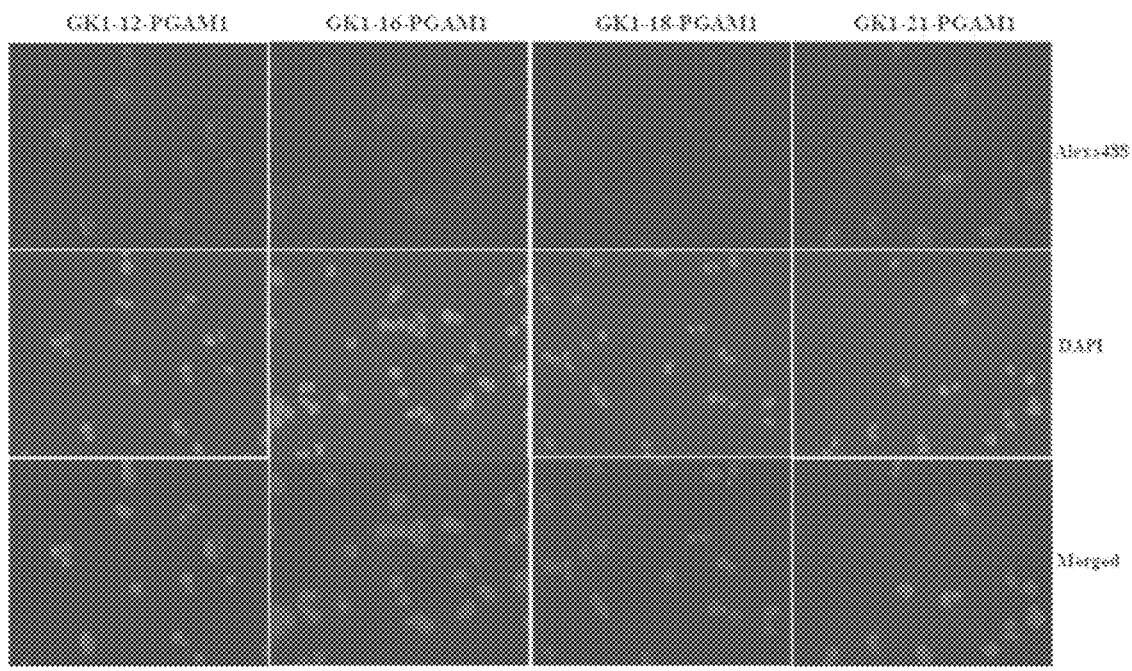

In order to confirm the intracellular locations of the cell-transduced fusion protein in which a GK1 derivative peptide fused with the PGAM1 protein, immunostaining was performed in the same manner as described above. The GK1 derivative peptides were also detected in the cytoplasm and nucleus. Among them, eight peptides having favorable cell transduction efficiency were selected, and are shown in FIGS. 5A and 5B.

In order to examine the cell protection effect of the fusion protein fused with the GK1 derivative peptide against oxidative stress, MTT analysis was performed in the same manner as described above. The cell viability, which had been reduced to 57% due to $H_2O_2$, was increased to the minimum value of 56% to the maximum value of 83% when pre-treatment was performed with the fusion protein in which the GK1 candidate protein was fused with the PGAM1 protein [FIG. 6]. In the case of the GK1-PGAM1 fusion protein, the cell viability was increased by 80%.

Table 1 below shows twenty-three specific examples of amino acid sequences of the protein transduction domain of the present disclosure. Further, Table 2 below shows nucleotide sequences encoding the twenty-three specific examples of the protein transduction domain of the present disclosure.

TABLE 1

| Name | Seq. No. | Peptide sequence |
|---|---|---|
| GK1 | 1 | AANDLAEGLAELADTVGV |
| GK1-1 | 2 | RANDLAEGLAELADTVGV |
| GK1-2 | 3 | RRNDLAEGLAELADTVGV |
| GK1-3 | 4 | RRRDLAEGLAELADTVGV |
| GK1-4 | 5 | AANDLAEGLAELADTVGR |
| GK1-5 | 6 | AANDLAEGLAELADTVRR |
| GK1-6 | 7 | AANDLAEGLAELADTRRR |
| GK1-7 | 8 | ARNDLAEGLAELADTVGV |
| GK1-8 | 9 | AARDLAEGLAELADTVGV |
| GK1-9 | 10 | AANDLAEGLAELADTVRV |
| GK1-10 | 11 | AANDLAEGLAELADTRGV |
| GK1-11 | 12 | RAANDLAEGLAELADTVGV |
| GK1-12 | 13 | RRAANDLAEGLAELADTVGV |
| GK1-13 | 14 | RRRAANDLAEGLAELADTVGV |
| GK1-14 | 15 | AANDLAEGLAELADTVGVR |
| GK1-15 | 16 | AANDLAEGLAELADTVGVRR |
| GK1-16 | 17 | AANDLAEGLAELADTVGVRRR |
| GK1-17 | 18 | RKKRRQRRRAANDLAEGLAELADTVGV |
| GK1-18 | 19 | AANDLAEGLAELADTVGVRKKRRQRRR |
| GK1-19 | 20 | KETWWETAANDLAEGLAELADTVGV |
| GK1-20 | 21 | EWSQPKKKRKVAANDLAEGLAELADTVGV |
| GK1-21 | 22 | AANDLAEGLAELADTVGVKETWWET |
| GK1-22 | 23 | AANDLAEGLAELADTVGVEWSQPKKKRKV |

TABLE 2

| Name | Seq. No. | Nucleotide sequence |
|---|---|---|
| GK1 | 24 | gct gcg aat gat ctt gcg gaa ggt ctg gcg gaa ctc gcg gat acg gta ggc gta |
| GK1-1 | 25 | cgc gcg aat gat ctt gcg gaa ggt ctg gcg gaa ctc gcg gat acg gta ggc gta |
| GK1-2 | 26 | cgc cgt aat gat ctt gcg gaa ggt ctg gcg gaa ctc gcg gat acg gta ggc gta |
| GK1-3 | 27 | cgc cgt cgc gat ctt gcg gaa ggt ctg gcg gaa ctc gcg gat acg gta ggc gta |
| GK1-4 | 28 | gct gcg aat gat ctt gcg gaa ggt ctg gcg gaa ctc gcg gat acg gta ggc cgc |
| GK1-5 | 29 | gct gcg aat gat ctt gcg gaa ggt ctg gcg gaa ctc gcg gat acg gta cgc cgc |
| GK1-6 | 30 | gct gcg aat gat ctt gcg gaa ggt ctg gcg gaa ctc gcg gat acg cgt cgc cgc |
| GK1-7 | 31 | gct cgc aat gat ctt gcg gaa ggt ctg gcg gaa ctc gcg gat acg gta ggc gta |
| GK1-8 | 32 | gct gcg cgc gat ctt gcg gaa ggt ctg gcg gaa ctc gcg gat acg gta ggc gta |
| GK1-9 | 33 | gct gcg aat gat ctt gcg gaa ggt ctg gcg gaa ctc gcg gat acg gta cgc gta |
| GK1-10 | 34 | gct gcg aat gat ctt gcg gaa ggt ctg gcg gaa ctc gcg gat acg cgc ggc gta |
| GK1-11 | 35 | cgc gct gcg aat gat ctt gcg gaa ggt ctg gcg gaa ctc gcg gat acg gta ggc gta |
| GK1-12 | 36 | cgc cgt gct gcg aat gat ctt gcg gaa ggt ctg gcg gaa ctc gcg gat acg gta ggc gta |
| GK1-13 | 37 | cgc cgt cgc gct gcg aat gat ctt gcg gaa ggt ctg gcg gaa ctc gcg gat acg gta ggc gta |
| GK1-14 | 38 | gct gcg aat gat ctt gcg gaa ggt ctg gcg gaa ctc gcg gat acg gta ggc gta cgc |
| GK1-15 | 39 | gct gcg aat gat ctt gcg gaa ggt ctg gcg gaa ctc gcg gat acg gta ggc gta cgc cgt |

TABLE 2-continued

| Name | Seq. No. | Nucleotide sequence |
|---|---|---|
| GK1-16 | 40 | gct gcg aat gat ctt gcg gaa ggt ctg gcg gaa ctc gcg gat acg gta ggc gta cgc cgt cgc |
| GK1-17 | 41 | agg aag aag agg aga cag cga cga aga gct gcg aat gat ctt gcg gaa ggt ctg gcg gaa ctc gcg gat acg gta ggc gta |
| GK1-18 | 42 | gct gcg aat gat ctt gcg gaa ggt ctg gcg gaa ctc gcg gat acg gta ggc gta agg aag aag agg aga cag cga cga aga |
| GK1-19 | 43 | aaa gaa acc tgg tgg gaa acc gct gcg aat gat ctt gcg gaa ggt ctg gcg gaa ctc gcg gat acg gta ggc gta |
| GK1-20 | 44 | gaa tgg tct cag ccg aaa aaa aaa cgt aaa gtg gct gcg aat gat ctt gcg gaa ggt ctg gcg gaa ctc gcg gat acg gta ggc gta |
| GK1-21 | 45 | gct gcg aat gat ctt gcg gaa ggt ctg gcg gaa ctc gcg gat acg gta ggc gta aaa gaa acc tgg tgg gaa acc |
| GK1-22 | 46 | gct gcg aat gat ctt gcg gaa ggt ctg gcg gaa ctc gcg gat acg gta ggc gta gaa tgg tct cag ccg aaa aaa aaa cgt aaa gtg |

Although embodiments of the present disclosure have been disclosed for illustrative purposes, those skilled in the art will appreciate that various modifications, additions and substitutions are possible, without departing from the scope and spirit of the disclosure as disclosed in the accompanying claims.

It is revealed that the present disclosure was carried out with the support of the Ministry of Science, Technology and Communication of the Republic of Korea (NRF-2018M3A9C8023568) and the Ministry of Education of the Republic of Korea (2019R1A6A11036849).

What is claimed is:

1. A protein transduction domain comprising a sequence selected from the group consisting of (A), (B) and (C) below, comprising 18 to 29 amino acids, wherein the protein transduction domain is chemically bonded to a cargo molecule to thus transport the cargo molecule into a mammalian cell or tissue:
(A) $(X_1X_2X_3)$-DLAEGLAELADT-$(X_4X_5X_6)$ (SEQ ID NO:49),
wherein $X_1$ is A or R, $X_2$ is A or R, $X_3$ is N or R, $X_4$ is V or R, $X_5$ is G or R, and $X_6$ is V or R,
(B) $(R_7)$-AANDLAEGLAELADTVGV (SEQ ID NO: 1) or AANDLAEGLAELADTVGV (SEQ ID NO: 1)-$(R_7)$,
wherein $R_7$ is R, RR, or RRR, and
(C) $(R_8)$-AANDLAEGLAELADTVGV (SEQ ID NO: 1) or AANDLAEGLAELADTVGV (SEQ ID NO: 1)-$(R_8)$,
wherein $R_8$ is RKKRRQRRR (SEQ ID NO: 54), KETWWET (SEQ ID NO: 55), or EWSQPKKKRKV (SEQ ID NO: 56).

2. The protein transduction domain of claim 1, wherein the protein transduction domain comprises a sequence selected from the group consisting of SEQ ID NOs: 1-23.

3. The protein transduction domain of claim 1, wherein the cargo molecule is selected from the group consisting of proteins, peptides, amino acids, nucleic acids, carbohydrates, lipids, and a mixture of one or more thereof.

4. The protein transduction domain of claim 1, wherein bonding between the cargo molecule and the protein transduction domain is covalent bonding or non-covalent bonding.

5. A fusion compound, which may penetrate into a mammalian cell or tissue, comprising:
a protein transduction domain comprising a sequence selected from the group consisting of (A), (B) and (C) below, comprising 18 to 29 amino acids, and is chemically bonded to cargo molecule for preventing or treating diseases to thus transport the cargo molecule into mammalian cell or tissue:
(A) $(X_1X_2X_3)$-DLAEGLAELADT-$(X_4X_5X_6)$ (SEQ ID NO:49),
wherein $X_1$ is A or R, $X_2$ is A or R, $X_3$ is N or R, $X_4$ is V or R, $X_5$ is G or R, and $X_6$ is V or R,
(B) $(R_7)$-AANDLAEGLAELADTVGV (SEQ ID NO: 1) or AANDLAEGLAELADTVGV (SEQ ID NO: 1)-$(R_7)$,
wherein $R_7$ is R, RR, or RRR, and
(C) $(R_8)$-AANDLAEGLAELADTVGV (SEQ ID NO: 1) or AANDLAEGLAELADTVGV (SEQ ID NO: 1)-$(R_8)$,
wherein $R_8$ is RKKRRQRRR (SEQ ID NO: 54), KETWWET (SEQ ID NO: 55), or EWSQPKKKRKV (SEQ ID NO: 56).

6. The fusion compound of claim 5, wherein the protein transduction domain comprises a sequence selected from the group consisting of SEQ ID NOs: 1-23.

7. The fusion compound of claim 5, wherein the cargo molecule is selected from the group consisting of proteins, peptides, amino acids, nucleic acids, carbohydrates, lipids, and a mixture of one or more thereof.

8. A method for treating disease in a subject, said method consisting of administering to said subject a therapeutically effective amount of the fusion compound of claim 5, wherein the fusion compound may penetrate into a mammalian cell or tissue.

9. A cosmetic composition comprising:
the fusion compound of claim 5, wherein the fusion compound may penetrate into a mammalian cell or tissue.

* * * * *

```
                        SEQUENCE LISTING

<160> NUMBER OF SEQ ID NOS: 57

<210> SEQ ID NO 1
<211> LENGTH: 18
<212> TYPE: PRT
<213> ORGANISM: Artificial Sequence
<220> FEATURE:
<223> OTHER INFORMATION: protein transducing domain

<400> SEQUENCE: 1

Ala Ala Asn Asp Leu Ala Glu Gly Leu Ala Glu Leu Ala Asp Thr Val
1               5                   10                  15

Gly Val

<210> SEQ ID NO 2
<211> LENGTH: 18
<212> TYPE: PRT
<213> ORGANISM: Artificial Sequence
<220> FEATURE:
<223> OTHER INFORMATION: protein transducing domain

<400> SEQUENCE: 2

Arg Ala Asn Asp Leu Ala Glu Gly Leu Ala Glu Leu Ala Asp Thr Val
1               5                   10                  15

Gly Val

<210> SEQ ID NO 3
<211> LENGTH: 18
<212> TYPE: PRT
<213> ORGANISM: Artificial Sequence
<220> FEATURE:
<223> OTHER INFORMATION: protein transducing domain GK1-2
```

<400> SEQUENCE: 3

Arg Arg Asn Asp Leu Ala Glu Gly Leu Ala Glu Leu Ala Asp Thr Val
1               5                   10                  15

Gly Val

<210> SEQ ID NO 4
<211> LENGTH: 18
<212> TYPE: PRT
<213> ORGANISM: Artificial Sequence
<220> FEATURE:
<223> OTHER INFORMATION: protein transducing domain GK1-3

<400> SEQUENCE: 4

Arg Arg Arg Asp Leu Ala Glu Gly Leu Ala Glu Leu Ala Asp Thr Val
1               5                   10                  15

Gly Val

<210> SEQ ID NO 5
<211> LENGTH: 18
<212> TYPE: PRT
<213> ORGANISM: Artificial Sequence
<220> FEATURE:
<223> OTHER INFORMATION: protein transducing domain GK1-4

<400> SEQUENCE: 5

Ala Ala Asn Asp Leu Ala Glu Gly Leu Ala Glu Leu Ala Asp Thr Val
1               5                   10                  15

Gly Arg

<210> SEQ ID NO 6
<211> LENGTH: 18
<212> TYPE: PRT
<213> ORGANISM: Artificial Sequence
<220> FEATURE:
<223> OTHER INFORMATION: protein transducing domain GK1-5

<400> SEQUENCE: 6

Ala Ala Asn Asp Leu Ala Glu Gly Leu Ala Glu Leu Ala Asp Thr Val
1               5                   10                  15

Arg Arg

<210> SEQ ID NO 7
<211> LENGTH: 18
<212> TYPE: PRT
<213> ORGANISM: Artificial Sequence
<220> FEATURE:
<223> OTHER INFORMATION: protein transducing domain GK1-6

<400> SEQUENCE: 7

Ala Ala Asn Asp Leu Ala Glu Gly Leu Ala Glu Leu Ala Asp Thr Arg
1               5                   10                  15

Arg Arg

<210> SEQ ID NO 8
<211> LENGTH: 18
<212> TYPE: PRT
<213> ORGANISM: Artificial Sequence
<220> FEATURE:
<223> OTHER INFORMATION: protein transducing domain GK1-7

```
<400> SEQUENCE: 8

Ala Arg Asn Asp Leu Ala Glu Gly Leu Ala Glu Leu Ala Asp Thr Val
1               5                   10                  15

Gly Val

<210> SEQ ID NO 9
<211> LENGTH: 18
<212> TYPE: PRT
<213> ORGANISM: Artificial Sequence
<220> FEATURE:
<223> OTHER INFORMATION: protein transducing domain GK1-8

<400> SEQUENCE: 9

Ala Ala Arg Asp Leu Ala Glu Gly Leu Ala Glu Leu Ala Asp Thr Val
1               5                   10                  15

Gly Val

<210> SEQ ID NO 10
<211> LENGTH: 18
<212> TYPE: PRT
<213> ORGANISM: Artificial Sequence
<220> FEATURE:
<223> OTHER INFORMATION: protein transducing domain GK1-9

<400> SEQUENCE: 10

Ala Ala Asn Asp Leu Ala Glu Gly Leu Ala Glu Leu Ala Asp Thr Val
1               5                   10                  15

Arg Val

<210> SEQ ID NO 11
<211> LENGTH: 18
<212> TYPE: PRT
<213> ORGANISM: Artificial Sequence
<220> FEATURE:
<223> OTHER INFORMATION: protein transducing domain GK1-10

<400> SEQUENCE: 11

Ala Ala Asn Asp Leu Ala Glu Gly Leu Ala Glu Leu Ala Asp Thr Arg
1               5                   10                  15

Gly Val

<210> SEQ ID NO 12
<211> LENGTH: 19
<212> TYPE: PRT
<213> ORGANISM: Artificial Sequence
<220> FEATURE:
<223> OTHER INFORMATION: protein transducing domain GK1-11

<400> SEQUENCE: 12

Arg Ala Ala Asn Asp Leu Ala Glu Gly Leu Ala Glu Leu Ala Asp Thr
1               5                   10                  15

Val Gly Val

<210> SEQ ID NO 13
<211> LENGTH: 20
<212> TYPE: PRT
<213> ORGANISM: Artificial Sequence
<220> FEATURE:
<223> OTHER INFORMATION: protein transducing domain GK1-12
```

<400> SEQUENCE: 13

Arg Arg Ala Ala Asn Asp Leu Ala Glu Gly Leu Ala Glu Leu Ala Asp
1               5                   10                  15

Thr Val Gly Val
            20

<210> SEQ ID NO 14
<211> LENGTH: 21
<212> TYPE: PRT
<213> ORGANISM: Artificial Sequence
<220> FEATURE:
<223> OTHER INFORMATION: protein transducing domain GK1-13

<400> SEQUENCE: 14

Arg Arg Arg Ala Ala Asn Asp Leu Ala Glu Gly Leu Ala Glu Leu Ala
1               5                   10                  15

Asp Thr Val Gly Val
            20

<210> SEQ ID NO 15
<211> LENGTH: 19
<212> TYPE: PRT
<213> ORGANISM: Artificial Sequence
<220> FEATURE:
<223> OTHER INFORMATION: protein transducing domain GK1-14

<400> SEQUENCE: 15

Ala Ala Asn Asp Leu Ala Glu Gly Leu Ala Glu Leu Ala Asp Thr Val
1               5                   10                  15

Gly Val Arg

<210> SEQ ID NO 16
<211> LENGTH: 20
<212> TYPE: PRT
<213> ORGANISM: Artificial Sequence
<220> FEATURE:
<223> OTHER INFORMATION: protein transducing domain GK1-15

<400> SEQUENCE: 16

Ala Ala Asn Asp Leu Ala Glu Gly Leu Ala Glu Leu Ala Asp Thr Val
1               5                   10                  15

Gly Val Arg Arg
            20

<210> SEQ ID NO 17
<211> LENGTH: 21
<212> TYPE: PRT
<213> ORGANISM: Artificial Sequence
<220> FEATURE:
<223> OTHER INFORMATION: protein transducing domain GK1-16

<400> SEQUENCE: 17

Ala Ala Asn Asp Leu Ala Glu Gly Leu Ala Glu Leu Ala Asp Thr Val
1               5                   10                  15

Gly Val Arg Arg Arg
            20

<210> SEQ ID NO 18
<211> LENGTH: 27
<212> TYPE: PRT
<213> ORGANISM: Artificial Sequence
<220> FEATURE:
<223> OTHER INFORMATION: protein transducing domain GK1-17

<400> SEQUENCE: 18

Arg Lys Lys Arg Arg Gln Arg Arg Ala Ala Asn Asp Leu Ala Glu
1               5                   10                  15

Gly Leu Ala Glu Leu Ala Asp Thr Val Gly Val
            20                  25

<210> SEQ ID NO 19
<211> LENGTH: 27
<212> TYPE: PRT
<213> ORGANISM: Artificial Sequence
<220> FEATURE:
<223> OTHER INFORMATION: protein transducing domain GK1-18

<400> SEQUENCE: 19

Ala Ala Asn Asp Leu Ala Glu Gly Leu Ala Glu Leu Ala Asp Thr Val
1               5                   10                  15

Gly Val Arg Lys Lys Arg Arg Gln Arg Arg Arg
            20                  25

<210> SEQ ID NO 20
<211> LENGTH: 25
<212> TYPE: PRT
<213> ORGANISM: Artificial Sequence
<220> FEATURE:
<223> OTHER INFORMATION: protein transducing domain GK1-19

<400> SEQUENCE: 20

Lys Glu Thr Trp Trp Glu Thr Ala Ala Asn Asp Leu Ala Glu Gly Leu
1               5                   10                  15

Ala Glu Leu Ala Asp Thr Val Gly Val
            20                  25

<210> SEQ ID NO 21
<211> LENGTH: 29
<212> TYPE: PRT
<213> ORGANISM: Artificial Sequence
<220> FEATURE:
<223> OTHER INFORMATION: protein transducing domain GK1-20

<400> SEQUENCE: 21

Glu Trp Ser Gln Pro Lys Lys Lys Arg Lys Val Ala Ala Asn Asp Leu
1               5                   10                  15

Ala Glu Gly Leu Ala Glu Leu Ala Asp Thr Val Gly Val
            20                  25

<210> SEQ ID NO 22
<211> LENGTH: 25
<212> TYPE: PRT
<213> ORGANISM: Artificial Sequence
<220> FEATURE:
<223> OTHER INFORMATION: protein transducing domain GK1-21

<400> SEQUENCE: 22

Ala Ala Asn Asp Leu Ala Glu Gly Leu Ala Glu Leu Ala Asp Thr Val
1               5                   10                  15

Gly Val Lys Glu Thr Trp Trp Glu Thr
            20                  25

<210> SEQ ID NO 23
<211> LENGTH: 29
<212> TYPE: PRT
<213> ORGANISM: Artificial Sequence
<220> FEATURE:

<223> OTHER INFORMATION: protein transducing domain GK1-22

<400> SEQUENCE: 23

Ala Ala Asn Asp Leu Ala Glu Gly Leu Ala Glu Leu Ala Asp Thr Val
1               5                   10                  15

Gly Val Glu Trp Ser Gln Pro Lys Lys Lys Arg Lys Val
            20                  25

<210> SEQ ID NO 24
<211> LENGTH: 54
<212> TYPE: DNA
<213> ORGANISM: Artificial Sequence
<220> FEATURE:
<223> OTHER INFORMATION: polynucleotide encoding protein transducing
      domain GK1

<400> SEQUENCE: 24
gctgcgaatg atcttgcgga aggtctggcg gaactcgcgg atacggtagg cgta          54

<210> SEQ ID NO 25
<211> LENGTH: 54
<212> TYPE: DNA
<213> ORGANISM: Artificial Sequence
<220> FEATURE:
<223> OTHER INFORMATION: polynucleotide encoding protein transducing
      domain GK1-1

<400> SEQUENCE: 25
cgcgcgaatg atcttgcgga aggtctggcg gaactcgcgg atacggtagg cgta          54

<210> SEQ ID NO 26
<211> LENGTH: 54
<212> TYPE: DNA
<213> ORGANISM: Artificial Sequence
<220> FEATURE:
<223> OTHER INFORMATION: polynucleotide encoding protein transducing
      domain GK1-2

<400> SEQUENCE: 26
cgccgtaatg atcttgcgga aggtctggcg gaactcgcgg atacggtagg cgta          54

<210> SEQ ID NO 27
<211> LENGTH: 54
<212> TYPE: DNA
<213> ORGANISM: Artificial Sequence
<220> FEATURE:
<223> OTHER INFORMATION: polynucleotide encoding protein transducing
      domain GK1-3

<400> SEQUENCE: 27
cgccgtcgcg atcttgcgga aggtctggcg gaactcgcgg atacggtagg cgta          54

<210> SEQ ID NO 28
<211> LENGTH: 54
<212> TYPE: DNA
<213> ORGANISM: Artificial Sequence
<220> FEATURE:
<223> OTHER INFORMATION: polynucleotide encoding protein transducing
      domain GK1-4

<400> SEQUENCE: 28
gctgcgaatg atcttgcgga aggtctggcg gaactcgcgg atacggtagg ccgc          54

<210> SEQ ID NO 29
<211> LENGTH: 54
<212> TYPE: DNA

```
<213> ORGANISM: Artificial Sequence
<220> FEATURE:
<223> OTHER INFORMATION: polynucleotide encoding protein transducing
      domain GK1-5

<400> SEQUENCE: 29
gctgcgaatg atcttgcgga aggtctggcg gaactcgcgg atacggtacg ccgc        54

<210> SEQ ID NO 30
<211> LENGTH: 54
<212> TYPE: DNA
<213> ORGANISM: Artificial Sequence
<220> FEATURE:
<223> OTHER INFORMATION: polynucleotide encoding protein transducing
      domain GK1-6

<400> SEQUENCE: 30
gctgcgaatg atcttgcgga aggtctggcg gaactcgcgg atacgcgtcg ccgc        54

<210> SEQ ID NO 31
<211> LENGTH: 54
<212> TYPE: DNA
<213> ORGANISM: Artificial Sequence
<220> FEATURE:
<223> OTHER INFORMATION: polynucleotide encoding protein transducing
      domain GK1-7

<400> SEQUENCE: 31
gctcgcaatg atcttgcgga aggtctggcg gaactcgcgg atacggtagg cgta        54

<210> SEQ ID NO 32
<211> LENGTH: 54
<212> TYPE: DNA
<213> ORGANISM: Artificial Sequence
<220> FEATURE:
<223> OTHER INFORMATION: polynucleotide encoding protein transducing
      domain GK1-8

<400> SEQUENCE: 32
gctgcgcgcg atcttgcgga aggtctggcg gaactcgcgg atacggtagg cgta        54

<210> SEQ ID NO 33
<211> LENGTH: 54
<212> TYPE: DNA
<213> ORGANISM: Artificial Sequence
<220> FEATURE:
<223> OTHER INFORMATION: polynucleotide encoding protein transducing
      domain GK1-9

<400> SEQUENCE: 33
gctgcgaatg atcttgcgga aggtctggcg gaactcgcgg atacggtacg cgta        54

<210> SEQ ID NO 34
<211> LENGTH: 54
<212> TYPE: DNA
<213> ORGANISM: Artificial Sequence
<220> FEATURE:
<223> OTHER INFORMATION: polynucleotide encoding protein transducing
      domain GK1-10

<400> SEQUENCE: 34
gctgcgaatg atcttgcgga aggtctggcg gaactcgcgg atacgcgcgg cgta        54

<210> SEQ ID NO 35
<211> LENGTH: 57
<212> TYPE: DNA
<213> ORGANISM: Artificial Sequence
```

```
<220> FEATURE:
<223> OTHER INFORMATION: polynucleotide encoding protein transducing
      domain GK1-11

<400> SEQUENCE: 35
cgcgctgcga atgatcttgc ggaaggtctg gcggaactcg cggatacggt aggcgta        57

<210> SEQ ID NO 36
<211> LENGTH: 60
<212> TYPE: DNA
<213> ORGANISM: Artificial Sequence
<220> FEATURE:
<223> OTHER INFORMATION: polynucleotide encoding protein transducing
      domain GK1-12

<400> SEQUENCE: 36
cgccgtgctg cgaatgatct tgcggaaggt ctggcggaac tcgcggatac ggtaggcgta    60

<210> SEQ ID NO 37
<211> LENGTH: 63
<212> TYPE: DNA
<213> ORGANISM: Artificial Sequence
<220> FEATURE:
<223> OTHER INFORMATION: polynucleotide encoding protein transducing
      domain GK1-13

<400> SEQUENCE: 37
cgccgtcgcg ctgcgaatga tcttgcggaa ggtctggcgg aactcgcgga tacggtaggc    60
gta                                                                  63

<210> SEQ ID NO 38
<211> LENGTH: 57
<212> TYPE: DNA
<213> ORGANISM: Artificial Sequence
<220> FEATURE:
<223> OTHER INFORMATION: polynucleotide encoding protein transducing
      domain GK1-14

<400> SEQUENCE: 38
gctgcgaatg atcttgcgga aggtctggcg gaactcgcgg atacggtagg cgtacgc        57

<210> SEQ ID NO 39
<211> LENGTH: 60
<212> TYPE: DNA
<213> ORGANISM: Artificial Sequence
<220> FEATURE:
<223> OTHER INFORMATION: polynucleotide encoding protein transducing
      domain GK1-15

<400> SEQUENCE: 39
gctgcgaatg atcttgcgga aggtctggcg gaactcgcgg atacggtagg cgtacgccgt    60

<210> SEQ ID NO 40
<211> LENGTH: 63
<212> TYPE: DNA
<213> ORGANISM: Artificial Sequence
<220> FEATURE:
<223> OTHER INFORMATION: polynucleotide encoding protein transducing
      domain GK1-16

<400> SEQUENCE: 40
gctgcgaatg atcttgcgga aggtctggcg gaactcgcgg atacggtagg cgtacgccgt    60
cgc                                                                  63

<210> SEQ ID NO 41
```

-continued

```
<211> LENGTH: 81
<212> TYPE: DNA
<213> ORGANISM: Artificial Sequence
<220> FEATURE:
<223> OTHER INFORMATION: polynucleotide encoding protein transducing
      domain GK1-17

<400> SEQUENCE: 41
aggaagaagc ggagacagcg acgaagagct gcgaatgatc ttgcggaagg tctggcggaa      60
ctcgcggata cggtaggcgt a                                                81

<210> SEQ ID NO 42
<211> LENGTH: 81
<212> TYPE: DNA
<213> ORGANISM: Artificial Sequence
<220> FEATURE:
<223> OTHER INFORMATION: polynucleotide encoding protein transducing
      domain GK1-18

<400> SEQUENCE: 42
gctgcgaatg atcttgcgga aggtctggcg gaactcgcgg atacggtagg cgtaaggaag      60
aagcggagac agcgacgaag a                                                81

<210> SEQ ID NO 43
<211> LENGTH: 75
<212> TYPE: DNA
<213> ORGANISM: Artificial Sequence
<220> FEATURE:
<223> OTHER INFORMATION: polynucleotide encoding protein transducing
      domain GK1-19

<400> SEQUENCE: 43
aaagaaacct ggtgggaaac cgctgcgaat gatcttgcgg aaggtctggc ggaactcgcg      60
gatacggtag gcgta                                                       75

<210> SEQ ID NO 44
<211> LENGTH: 87
<212> TYPE: DNA
<213> ORGANISM: Artificial Sequence
<220> FEATURE:
<223> OTHER INFORMATION: polynucleotide encoding protein transducing
      domain GK1-20

<400> SEQUENCE: 44
gaatggtctc agccgaaaaa aaaacgtaaa gtggctgcga atgatcttgc ggaaggtctg      60
gcggaactcg cggatacggt aggcgta                                          87

<210> SEQ ID NO 45
<211> LENGTH: 75
<212> TYPE: DNA
<213> ORGANISM: Artificial Sequence
<220> FEATURE:
<223> OTHER INFORMATION: polynucleotide encoding protein transducing
      domain GK1-21

<400> SEQUENCE: 45
gctgcgaatg atcttgcgga aggtctggcg gaactcgcgg atacggtagg cgtaaaagaa      60
acctggtggg aaacc                                                       75

<210> SEQ ID NO 46
<211> LENGTH: 87
<212> TYPE: DNA
<213> ORGANISM: Artificial Sequence
<220> FEATURE:
```

<223> OTHER INFORMATION: polynucleotide encoding protein transducing
      domain GK1-22

<400> SEQUENCE: 46
gctgcgaatg atcttgcgga aggtctggcg gaactcgcgg atacggtagg cgtagaatgg    60
tctcagccga aaaaaaaacg taaagtg                                        87

<210> SEQ ID NO 47
<211> LENGTH: 60
<212> TYPE: DNA
<213> ORGANISM: Artificial Sequence
<220> FEATURE:
<223> OTHER INFORMATION: sense oligonucleotide

<400> SEQUENCE: 47
tatggctgcg aatgatcttg cggaaggtct ggcggaactc gcggatacgg taggcgtaca    60

<210> SEQ ID NO 48
<211> LENGTH: 60
<212> TYPE: DNA
<213> ORGANISM: Artificial Sequence
<220> FEATURE:
<223> OTHER INFORMATION: antisense oligonucleotide

<400> SEQUENCE: 48
tatgtacgcc taccgtatcc gcgagttccg ccagaccttc cgcaagatca ttcgcagcca    60

<210> SEQ ID NO 49
<211> LENGTH: 18
<212> TYPE: PRT
<213> ORGANISM: Artificial Sequence
<220> FEATURE:
<223> OTHER INFORMATION: peptide
<220> FEATURE:
<221> NAME/KEY: VARIANT
<222> LOCATION: (1)..(1)
<223> OTHER INFORMATION: Xaa is Ala or Arg
<220> FEATURE:
<221> NAME/KEY: VARIANT
<222> LOCATION: (2)..(2)
<223> OTHER INFORMATION: Xaa is Ala or Arg
<220> FEATURE:
<221> NAME/KEY: VARIANT
<222> LOCATION: (3)..(3)
<223> OTHER INFORMATION: Xaa is Asn or Arg
<220> FEATURE:
<221> NAME/KEY: VARIANT
<222> LOCATION: (16)..(16)
<223> OTHER INFORMATION: Xaa is Val or Arg
<220> FEATURE:
<221> NAME/KEY: VARIANT
<222> LOCATION: (17)..(17)
<223> OTHER INFORMATION: Xaa is Gly or Arg
<220> FEATURE:
<221> NAME/KEY: VARIANT
<222> LOCATION: (18)..(18)
<223> OTHER INFORMATION: Xaa is Val or Arg

<400> SEQUENCE: 49

Xaa Xaa Xaa Asp Leu Ala Glu Gly Leu Ala Glu Leu Ala Asp Thr Xaa
1               5                   10                  15

Xaa Xaa

<210> SEQ ID NO 50
<211> LENGTH: 9
<212> TYPE: PRT
<213> ORGANISM: Artificial Sequence
<220> FEATURE:
<223> OTHER INFORMATION: Peptide

<400> SEQUENCE: 50

Arg Lys Lys Arg Arg Gln Arg Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Peptide

<400> SEQUENCE: 51

Lys Glu Thr Trp Trp Glu Thr
1               5

<210> SEQ ID NO 52
<211> LENGTH: 11
<212> TYPE: PRT
<213> ORGANISM: Artificial Sequence
<220> FEATURE:
<223> OTHER INFORMATION: Peptide

<400> SEQUENCE: 52

Glu Trp Ser Gln Pro Lys Lys Arg Lys Val
1               5                   10

<210> SEQ ID NO 53
<211> LENGTH: 12
<212> TYPE: PRT
<213> ORGANISM: Artificial Sequence
<220> FEATURE:
<223> OTHER INFORMATION: peptide

<400> SEQUENCE: 53

Asp Leu Ala Glu Gly Leu Ala Glu Leu Ala Asp Thr
1               5                   10

<210> SEQ ID NO 54
<211> LENGTH: 9
<212> TYPE: PRT
<213> ORGANISM: Artificial Sequence
<220> FEATURE:
<223> OTHER INFORMATION: peptide

<400> SEQUENCE: 54

Arg Lys Lys Arg Arg Gln Arg Arg
1               5

<210> SEQ ID NO 55
<211> LENGTH: 7
<212> TYPE: PRT
<213> ORGANISM: Artificial Sequence
<220> FEATURE:
<223> OTHER INFORMATION: peptide

<400> SEQUENCE: 55

Lys Glu Thr Trp Trp Glu Thr
1               5

<210> SEQ ID NO 56
<211> LENGTH: 11
<212> TYPE: PRT
<213> ORGANISM: Artificial Sequence
<220> FEATURE:
<223> OTHER INFORMATION: peptide

```
<400> SEQUENCE: 56

Glu Trp Ser Gln Pro Lys Lys Lys Arg Lys Val
1               5                   10

<210> SEQ ID NO 57
<211> LENGTH: 21
<212> TYPE: PRT
<213> ORGANISM: Artificial Sequence
<220> FEATURE:
<223> OTHER INFORMATION: peptide

<400> SEQUENCE: 57

Lys Glu Thr Trp Trp Glu Thr Trp Trp Thr Glu Trp Ser Gln Pro Lys
1               5                   10                  15

Lys Lys Arg Lys Val
            20
```